(12) United States Patent
McGhie et al.

(10) Patent No.: US 9,101,347 B2
(45) Date of Patent: Aug. 11, 2015

(54) COAXIAL INCISIONAL FULL-CORE BIOPSY NEEDLE

(71) Applicant: Cook Medical Technologies LLC, Bloomington, IN (US)

(72) Inventors: Thomas W. McGhie, Bloomington, IN (US); Michael W. Hardert, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/744,454

(22) Filed: Jan. 18, 2013

(65) Prior Publication Data

US 2013/0131548 A1    May 23, 2013

Related U.S. Application Data

(63) Continuation of application No. PCT/US2011/045265, filed on Jul. 26, 2011.

(60) Provisional application No. 61/369,126, filed on Jul. 30, 2010.

(51) Int. Cl.
| | |
|---|---|
| *A61B 10/00* | (2006.01) |
| *A61B 10/02* | (2006.01) |
| *A61B 17/02* | (2006.01) |
| *A61B 17/04* | (2006.01) |

(52) U.S. Cl.
CPC .......... *A61B 10/0233* (2013.01); *A61B 10/0266* (2013.01); *A61B 10/0275* (2013.01); *A61B 17/0218* (2013.01); *A61B 17/0482* (2013.01)

(58) Field of Classification Search
CPC ....................................... A61B 5/00
USPC .......... 600/562, 564, 566, 567, 568
See application file for complete search history.

(56) References Cited

U.S. PATENT DOCUMENTS

| | | | |
|---|---|---|---|
| 4,785,826 A | | 11/1988 | Ward |
| 5,318,589 A | * | 6/1994 | Lichtman ...................... 606/205 |
| 5,331,971 A | * | 7/1994 | Bales et al. ................... 600/564 |

(Continued)

FOREIGN PATENT DOCUMENTS

| | | |
|---|---|---|
| WO | WO 96/27330 A1 | 9/1996 |
| WO | WO 02/07602 A2 | 1/2002 |

(Continued)

*Primary Examiner* — Rene Towa
*Assistant Examiner* — May Abouelela
(74) *Attorney, Agent, or Firm* — Woodard, Emhardt, Moriarty, McNett & Henry LLP (57) ABSTRACT

Among other things, there are disclosed embodiments of full-core biopsy needles having an outer needle component and a middle cannula through a lumen in the outer component, through which a mandrel may be placed. The outer component includes an internal boss that reduces its internal diameter, and the cannula includes fingers that extend distally. When the needle is inserted for biopsy, tissue enters the outer component and cannula. Moving the cannula forward causes the fingers to engage a surface of the internal boss, resulting in the fingers curving into the tissue. The fingers pinch the tissue while reducing or eliminating compression of the sample to provide an easier removal of the tissue from adjacent tissue, as well as providing a block or backstop keeping the tissue within the needle. Gaps are provided between the fingers to further reduce damage to the tissue sample.

14 Claims, 4 Drawing Sheets

(56) References Cited

U.S. PATENT DOCUMENTS

| | | | |
|---|---|---|---|
| 5,357,974 A * | 10/1994 | Baldridge | 600/567 |
| 5,423,330 A * | 6/1995 | Lee | 600/566 |
| 5,462,062 A * | 10/1995 | Rubinstein et al. | 600/567 |
| 5,542,432 A * | 8/1996 | Slater et al. | 600/564 |
| 5,595,186 A * | 1/1997 | Rubinstein et al. | 600/567 |
| 5,885,226 A * | 3/1999 | Rubinstein et al. | 600/564 |
| 5,910,121 A * | 6/1999 | Paolo et al. | 600/562 |
| 6,063,037 A * | 5/2000 | Mittermeier et al. | 600/567 |
| 6,080,115 A * | 6/2000 | Rubinstein | 600/567 |
| 6,110,127 A * | 8/2000 | Suzuki | 600/565 |
| 6,416,484 B1 * | 7/2002 | Miller et al. | 600/564 |
| 6,497,651 B1 * | 12/2002 | Kan et al. | 600/114 |
| 6,517,498 B1 * | 2/2003 | Burbank et al. | 600/564 |
| 6,572,563 B2 * | 6/2003 | Ouchi | 600/564 |
| 6,632,182 B1 * | 10/2003 | Treat | 600/564 |
| 6,827,692 B2 * | 12/2004 | Castellacci | 600/567 |
| 6,976,968 B2 * | 12/2005 | Ritchart et al. | 600/567 |
| 7,207,950 B2 * | 4/2007 | Goldenberg | 600/562 |
| 7,722,548 B2 * | 5/2010 | Cervi | 600/564 |
| 8,211,116 B2 * | 7/2012 | Oostman et al. | 606/133 |
| 8,444,656 B2 * | 5/2013 | Tippett | 606/133 |
| 2001/0005778 A1 * | 6/2001 | Ouchi | 600/564 |
| 2001/0014778 A1 * | 8/2001 | Worm et al. | 600/564 |
| 2002/0120212 A1 * | 8/2002 | Ritchart et al. | 600/567 |
| 2005/0049520 A1 * | 3/2005 | Nakao | 600/562 |
| 2005/0137585 A1 * | 6/2005 | Landman et al. | 606/1 |
| 2005/0267383 A1 * | 12/2005 | Groenke et al. | 600/567 |
| 2006/0224084 A1 * | 10/2006 | Vetter et al. | 600/567 |
| 2008/0045858 A1 * | 2/2008 | Tessitore et al. | 600/567 |
| 2008/0103410 A1 * | 5/2008 | Karpiel | 600/564 |
| 2008/0234602 A1 * | 9/2008 | Oostman et al. | 600/564 |
| 2010/0030108 A1 * | 2/2010 | Anderson et al. | 600/567 |
| 2010/0076343 A1 * | 3/2010 | Vetter et al. | 600/567 |
| 2010/0204610 A1 * | 8/2010 | Santiago Soriano Romero | 600/564 |
| 2010/0204611 A1 * | 8/2010 | Zambelli | 600/567 |
| 2011/0208089 A1 * | 8/2011 | Sundheimer et al. | 600/567 |
| 2012/0010527 A1 * | 1/2012 | Sundheimer et al. | 600/566 |
| 2012/0150066 A1 * | 6/2012 | Goldenberg | 600/562 |
| 2012/0157880 A1 * | 6/2012 | Haselby et al. | 600/567 |

FOREIGN PATENT DOCUMENTS

| WO | WO 2006/108100 A2 | 10/2006 |
|---|---|---|
| WO | WO 2008/027829 A2 | 3/2008 |

* cited by examiner

COAXIAL INCISIONAL FULL-CORE BIOPSY NEEDLE

STATEMENT OF RELATED APPLICATIONS

This application is a continuation of International Patent Application PCT/US2011/045265, filed Jul. 26, 2011, which claims the benefit of priority of U.S. Provisional Patent Application Ser. No. 61/369,126 filed Jul. 30, 2010, each of which is incorporated herein by reference in its entirety.

This disclosure concerns devices for obtaining a tissue sample in biopsy. In particular, it concerns devices able to obtain a full-circular core of tissue with improved results over existing devices.

BACKGROUND

It is often desirable to perform a biopsy to sample selected tissue from a patient for medical evaluation. For example, biopsies can be useful in diagnosing various forms of cancer and other diseases affecting a localized area of tissue. However, many existing biopsy devices use only about half or less of their diameter to obtain tissue. Other devices that obtain a full cylinder or "full core" of tissue have difficulty in withdrawing tissue, and/or in maintaining the physical state of the tissue so as to provide an accurate assessment of tissue condition. With respect to the latter difficulty, one desire in obtaining tissue samples is to obtain the tissue with minimal physical changes, such as from scoring or mashing by the device. Physical characteristics of tissue, such as placement or orientation of cells or tissue, may be as important or more important than the chemical or biological characteristics (e.g. presence of malignant cells or by-products).

Accordingly, there is a need for a biopsy apparatus and method that are better able to provide samples that are easier to study.

SUMMARY

Among other things, there is shown and described a full-core biopsy needle that includes an outer tubular component and a middle cannula. In particular embodiments, the outer tubular component has a body portion, a tip portion and a lumen through them, with the tip portion having a conical tapered outer surface extending entirely around the longitudinal axis of the component. The component has a portion joining the body and tip that is rounded externally and forms a boss within the lumen, so that the lumen has a first diameter proximal of the boss and a second smaller diameter distal of the boss, and that second smaller diameter of the lumen extending through the tip. The middle cannula has body portion and a tip portion in particular embodiments, with the tip portion having a plurality of fingers, at least two which are separated by a gap. The cannula is within the lumen of the outer component, and the component and cannula have first and second relative positions. The first relative position is one in which the fingers of the cannula are proximal of the boss in the outer component. The cannula can be moved distally with respect to the outer component to the second relative position, which may be the limit of possible distal movement of the cannula with respect to the component. That second relative portion is one in which at least two of the fingers are deflected inward by the boss so that they point toward each other but do not close the entirety of the gap between them.

A number of other features can be included. For example, an internal mandrel can extend through and slide with respect to the cannula and outer component between a first limit in which the mandrel's tip portion extends from the outer component's tip and a second limit in which the mandrel's tip is proximal of the cannula's fingers by a predetermined distance prior to movement of the fingers with respect to the outer component. The boss and rounded external part of the outer component may be substantially radially aligned, and the cannula's fingers can each have a respective external surface that is parallel to the cannula's longitudinal axis when they are in the second relative position. The external surface of the fingers have a constant external diameter throughout their length, which is the same as the external diameter of the body or other parts of the cannula. The fingers' distal portions have an internal diameter and an external diameter measured between them, and in certain embodiments the external diameter is the same as the external diameter of the cannula and the internal diameter is larger than the inner diameter of the cannula's lumen. In such cases the fingers are internally thinned, and are thinner than the wall of the cannula, with an enlargement of the lumen of the cannula at its distal end.

As further examples, some or all of the fingers may have respective edges that together form a continuous substantially part-elliptical path, and the fingers may individually come to a point and/or have distal linear or curvilinear edges. The boss of the outer component can include a surface that is substantially perpendicular to the longitudinal axis, and/or a surface that is angled at approximately 45 degrees to the longitudinal axis. The gap between fingers may be substantially elliptical, with a vertex of the substantially elliptical gap being between proximal portions of the fingers, and when the outer component and cannula are in the second relative position a portion of the gap adjacent that vertex remains open. The fingers can contact each other when the cannula and outer component are in the second relative position while a portion of the gap between them is open, and such contact can be at or adjacent the fingers' distal ends. The fingers may be smaller than at least one gap between them.

In other embodiments, a full-core biopsy needle can include an outer tubular component with a body portion, a transition portion, and a tip portion. The body portion has a substantially constant inner and outer diameter, and the transition portion curves inward from the body portion inner and outer diameter and forms an external rounded surface and an internal boss. The tip portion has a constant inner diameter that is smaller than the body portion's inner diameter and an outer surface that tapers so that the tip has a first thickness adjacent the transition portion and a distal edge. The outer component has a lumen through the body, transition and tip portions. A cannula is within the outer component's lumen and has a proximal portion and a distal portion. The cannula's proximal portion has substantially constant inner and outer diameters, and its distal portion has at least a first and second finger separated by a substantially elliptical gap. The outer component and the cannula have a first relative position with the cannula's fingers proximal of the outer component's boss, and they are adapted to be moved with respect to each other into a second relative position that is the limit of possible distal location of the cannula with respect to the outer component. In that second relative position, at least the first and second fingers are deflected inward by the boss, so that at least a portion of the first and second fingers point toward each other but do not close the entirety of the gap.

In certain embodiments, the fingers do not contact each other in that second relative position, and they may be pointed or have a distal flat or planar edge. The cannula may have at least four fingers equidistantly spaced. The boss may be substantially perpendicular to the longitudinal axis of the outer component, with the boss forcing the fingers in a direction substantially perpendicular to the longitudinal axis. The inner diameter of the outer component may be surrounded by a wall that curves into the boss. The fingers each have a distal end, and force may be applied by the boss on the fingers initially solely at their distal ends. The inward deflection of the fingers does not compress tissue within them around the whole diameter of such tissue. The fingers may each have a distal end edge, and substantially all compression on tissue within the fingers is exerted by those distal end edges. The length of respective travel of the cannula and outer component in going from the first to the second relative position can be less than the length of said fingers, e.g. not greater than half the length of said fingers.

These and other features may be found in a full-core biopsy needle as taught in this disclosure. Such needles can be much simpler in construction and use than existing products, at least because they are without complicated parts endemic to other devices, and provide less opportunity than other products for scoring or other injury to tissue along or adjacent to the biopsy path. The embodiments illustrated herein can be designed to generate a larger core sample of tissue, and do so with a minimal diameter needle so as to decrease the width of biopsy path (and resultant tissue damage and discomfort) needed to obtain a desired width of tissue sample.

DESCRIPTION OF THE ILLUSTRATED EMBODIMENTS

Reference will now be made to certain embodiments and specific language will be used to describe the same. It will nevertheless be understood that no limitation of the scope of this disclosure and the claims is thereby intended, such alterations, further modifications and further applications of the principles described herein being contemplated as would normally occur to one skilled in the art to which this disclosure relates.

Referring now to the Figures, there are shown embodiments of a biopsy needle 20 capable of full-core coaxial incisional biopsy. The illustrated embodiments of needle 20 include an outer needle component 22, a middle cannula component 24, and an inner mandrel component 26. A handle 28 is shown, connected at least to components 22 and 24, as discussed further below. Components 22, 24 and 26 are coaxially arranged, with mandrel 26 being within cannula 24 and cannula 24 being within needle 22. As will be described further, each component is slidable with respect to the others.

Outer component 22 is a substantially cylindrical elongated member in the illustrated embodiments. A proximal portion 30 is attached to handle 28, and distal portion 32 is inserted into the patient during a biopsy procedure. The wall 33 of needle 22 is of substantially a uniform thickness and uniform outer diameter throughout proximal portion 30 and much of distal portion 32, narrowing toward or in tip 40 as further noted below. A lumen 36 is bounded by the inner diameter of wall 33 and extends throughout needle 20.

Figure 2:
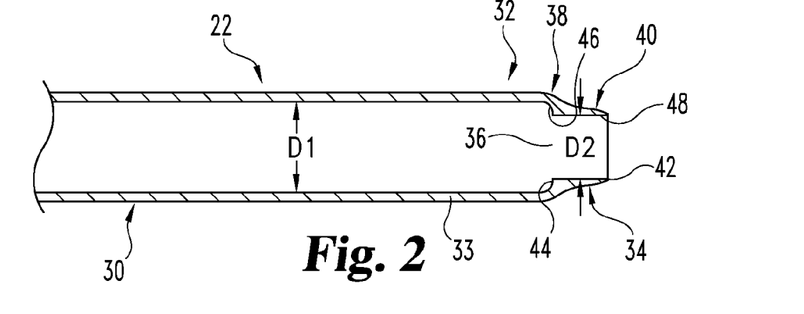
FIG. 2 is a side cross-sectional view of an embodiment of an outer component as indicated in FIG. 1.

End 34 of needle component 22 is configured for easy insertion into the skin and other soft tissues of a biopsy patient. Approaching end 34 on the exterior, wall 33 has a rounded portion 38 that reduces the outer diameter, and a tapered tip 40 ending in a distal edge 42. In a particular embodiment seen in FIG. 2, wall 33 turns inward while remaining at the uniform thickness, so that portion 38 is a rounded corner between a portion of wall 33 along the axis of lumen 36 and a portion of wall 33 substantially perpendicular to the axis of lumen 36. That embodiment also shows rounded portion 38 as having a substantially constant radius, so that a cross section of rounded portion 38 in a plane including the longitudinal axis is an arc of a circle, e.g. one quarter of a circle. Rounded portion 38 is convex in cross-section in this embodiment, and may meet the tapered surface of tip 40 in a corner or angle (as illustrated), or in a smooth concave curve. The proximal-most portion of tip 40 has approximately the same width as the rest of component 22, and it tapers linearly to edge 42. From edge 42, tip 40 widens uniformly toward rounded portion 38 and becomes the constant-width wall 33.

Lumen 36 has a first inner diameter D1 throughout most of needle component 22, and a second, smaller inner diameter D2 within tip 40. An inward turn of wall 30 corresponding to external rounded portion 38 forms a boss or flange 44 with a surface 46 that faces proximally along the axis of lumen 36. Surface 46 is the portion of wall 33 noted above that is perpendicular to the longitudinal axis in this embodiment. The portion of outer component 22 including rounded portion 38 and boss 44 may be thought of as a transition portion between proximal part 30 and tip 40. It will be seen that the length of boss or flange 44 is half of the difference between D1 and D2 in this embodiment. The thickness of tip 40 at the junction of rounded portion 38 and the linear taper is approximately the same as the length of boss or flange 44. Tip 40 has an inner surface 48 that surrounds the portion of lumen 36 through tip 40, and inner surface 48 is centered on the longitudinal axis of needle component 22, as is the larger-diameter inner wall around the rest of lumen 36. Surface 46 curves into that larger-diameter inner wall along the curve of rounded portion 38, also in an arc of a circle in cross-section in this embodiment, and surface 46 forms a corner with surface 48. The illustrated embodiment shows boss or flange 44 substantially perpendicular to surface 48, to the internal surface around lumen 36 in proximal portion 30, and to the longitudinal axis of needle component 22. As will be discussed further, edge 42 of tip 40 provides cutting and/or separation of tissue as needle 22 is advanced into the patient, with the taper of tip 40 gradually spreading the profile or gap made by edge 42. Rounded portion 38 provides an additional blunt or non-antagonistic (e.g. non-cutting, non-abrading or non-scoring) spreading of the tissue.

Figure 3:
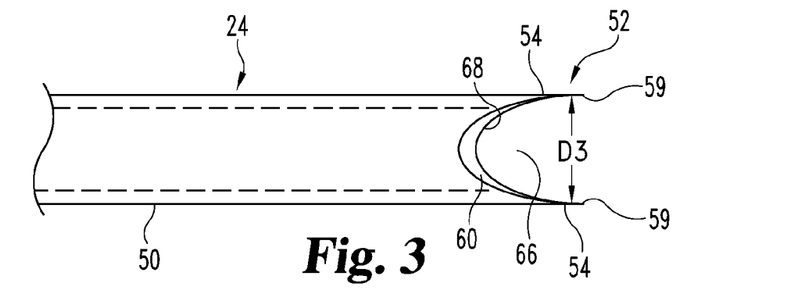
FIG. 3 is a side plan view of a portion of an embodiment of a middle cannula as indicated in FIG. 1.
Figure 4:
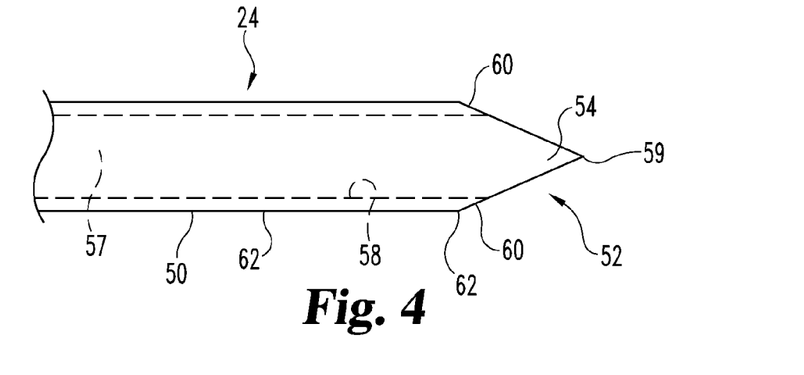
FIG. 4 is a top view of the portion shown in FIG. 3.
Figure 5:
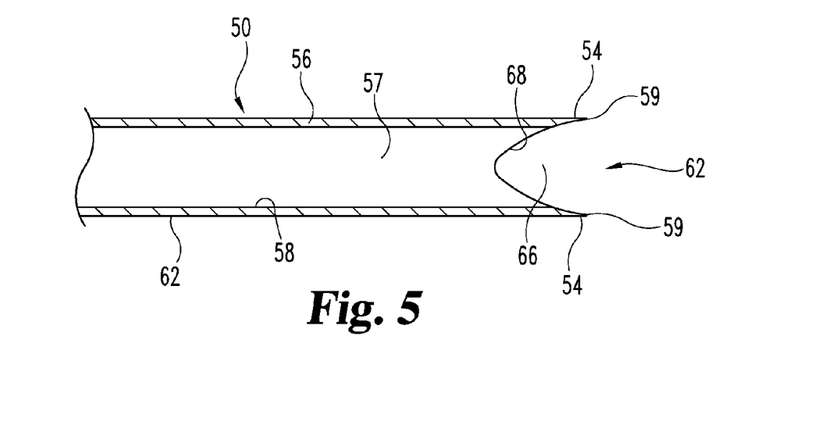
FIG. 5 is a side cross-sectional view of the portion shown in FIG. 3.

Middle cannula 24 has a substantially cylindrical main body 50 in this embodiment, which ends in a distal tip 52, which has two flexible fingers 54 extending distally in the embodiment shown in FIGS. 3-4. It will be understood that a different number of fingers may be provided, likewise equidistantly spaced or otherwise configured. Like outer needle component 22, the thickness of wall 56 of body 50 is thin, so as to minimize the overall diameter of needle 20 and/or make needle 20 no more bulky than prior biopsy needles with a single cannula. For example, particular embodiments have a thickness of wall 56 that is between about one-quarter and three-quarters the difference between the inner diameters D1 and D2 of needle component 22, or in a particular embodiment about half the difference between D1 and D2. Lumen 57 extends through body 50 and tip 52, and is bounded by a cylindrical wall 58 with a substantially uniform diameter. In a particular embodiment, fingers 54 are formed by cutting body 50 along a plane oblique to the longitudinal axis of cannula 24 (e.g. by grinding or laser cutting), resulting in points 59 in the illustrated embodiment, with planar U-shaped (e.g. a portion of a cylindric section forming part of an ellipse) surfaces 60 between points 59. Each surface 60 is continuous between adjacent fingers 54 or points 59 and are in one plane oblique to the longitudinal axis. Surfaces 60 extend between the outer surface 62 of body 50 and the inner wall 58 (which surrounds lumen 57) in cannula 24. Gaps 66, like surfaces 60 that partially surround them, have essentially the shape of a portion of an ellipse, as they reflect the intersection of a plane with a right circular cylinder. Accordingly, when fingers 54 are driven together, as further described below, one or more openings remain on the sides of cannula 24 next to the vertex of the elliptical gap 66 (at or adjacent the root of neighboring fingers 54) because of the shape and position of gaps 66 and surfaces 60. Each surface 60 thickens linearly (measured normal to the longitudinal axis) from an edge 68 bordering a respective gap 66 to the substantially uniform thickness of body 50.

Points 59 are not only tapered as viewed from the top (e.g. FIG. 4), i.e. tapered in width, but are also tapered as viewed from the side, i.e., radially or in the thickness of wall 56 (e.g. FIG. 3). While wall 56 has a substantially uniform thickness through body 50, that thickness lessens as the tip of each point 59 is approached. The outer diameter measured across fingers 54 is the same as the outer diameter of body 50. An inner diameter measured between fingers 54 toward points 59 (e.g. D3) is greater than the inner diameter of body 50. Fingers 54 are thus thinned from the inside. In that embodiment, the tapering thinness of points 59 provide easy bending of points 58, and the potential for bending at multiple portions or continuously along a portion, as will be discussed further below. Further, points 59 and the rest of fingers 54 do not interfere with, and in fact encourage, entry of tissue from tip 40 into cannula 24.

This embodiment of cannula 24 in FIGS. 3-4 has an outer diameter of body 50 and across fingers 54 that is substantially the same as the inner diameter D1 of lumen 36, to provide a close fit and slidability within outer needle component 22. The thickness of wall 56 of cannula 24 is approximately the same as the length of flange 44 of needle component 22. Accordingly, the diameter of lumen 57 of cannula 24 is substantially the same as the inner diameter D2 of tip 40 of component 22. A passage exists through tip 40 and lumen 57 of substantially constant diameter D2, except for a small enlargement or space 70 (FIGS. 1A, 6) adjacent flange 44 and points 59 due to the inner tapered thickness of fingers 54 out to points 59. Enlargement 70 has a maximum diameter of D1 of needle component 22. In a particular embodiment, the thickness of wall 56 in body 50 is approximately the same as that of wall 33 of outer needle component 22. Thus, fingers 54 are outside of the diameter of a tissue sample that would enter needle 20, and do not interfere with such tissue entry.

Inner mandrel component 26 is a solid elongated rod in this embodiment, while in other embodiments mandrel 26 could be at least partially hollow. Mandrel 26 has a diameter that is approximately the same as or slightly less than the inner diameter of lumen 57 of cannula 24, and a distal end 74 that is tapered to a point 76. In the illustrated embodiment, the taper of end 74 is such that a conical surface of end 74 has a greater angle with respect to the longitudinal axis of needle 20 than the exterior tapered surface of tip 40 of outer component 22. In other embodiments, the taper angle of end 74 may be such that a conical surface is substantially parallel or have a smaller angle than to the tapered exterior surface of tip 40. Mandrel 26 slides within cannula component 24, and in the illustrated embodiment has a close and slidable fit similar to that between cannula 24 and outer member 22. The illustrated embodiment of mandrel 26 has a forward-most position (seen in FIGS. 1, 1A, 1B) at which the beginning of the taper of end 74 is approximately even with the end of tip 40 of component 22, and a rearward-most position (seen in FIGS. 6-7) in which end 74 is a predetermined distance proximal of its forward-most position. The predetermined distance is the approximate length of core tissue sample desired to be taken.

Handle 28 is fixed to each of outer component 22 and middle cannula 24 at their respective proximal ends, with middle cannula 24 within outer component 22 and being slidable with respect to each other. In particular embodiments, mandrel 26 is connected to handle 28, or may be separate from handle 28 but inserted through handle 28 and into lumen 57 of cannula 24. An example of a handle structure that may be used in needle 20 is identical or similar to that currently used with QUICK-CORE® products sold by Cook Medical (Bloomington, Ind.). Embodiments of suitable handle structure are shown in U.S. Provisional Application No. 61/261,857, filed on Nov. 17, 2009, the entirety of which is incorporated herein by reference. Such handles 28 permit insertion into the body of needle 20 substantially in the form seen in FIG. 1, a cocking step in which outer component 22 and cannula 24 (or at least component 22) is primed or prepared for firing forward (e.g. FIGS. 1A, 1B), a firing step in which the combination of component 22 and cannula 24 (or at least outer component 22) are released to move forward rapidly over mandrel 26 to cut a cylindrical profile into tissue, with tissue entering tip 40 and lumen 36, 57 of component 22 and cannula 24 (e.g. FIG. 6), and an extension or gripping step in which cannula 24 is moved forward with respect to outer component 22 (e.g. FIG. 7). The cocking step may be performed by holding finger grips 80 and pulling back on plunger 82. Firing component 22 and cannula 24 is accomplished while holding finger grips 80 by forcing plunger 82 forward to overcome the cocked state, and may be accomplished by the same hand that holds finger grips 80. Moving cannula 24 forward inside component 22 is done by pressing forward plunger 82 (or another actuator on handle 28) once needle 20 is in the fired state.

In the illustrated embodiment, component 22, cannula 24 and mandrel 26 have an insertion configuration (FIG. 1A, 1B) which is seen during initial insertion of needle 20 into the patient. In that configuration, cannula 24 and component 22 have a first relative position in which points 59 of cannula 24 are proximal or rearward of surface 46 of boss 44 in component 22 (e.g., FIGS. 1A, 6), and tip 74 of mandrel 26 extends at least slightly from tip 40 of component 22. In that first relative position, the outer surfaces of fingers 54 are aligned with the longitudinal axis so that lumen 57 of cannula 24 communicates in a passage with lumen 36 through tip 40, with that passage of the inner diameter of cannula 24 of approximately uniform diameter (e.g. D2) except where enlarged adjacent fingers 54. Point 76 of mandrel 26 leads needle 20 during initial insertion into the patient, moving tissue to the side so that little or no tissue enters tip 40 during such insertion.

Figure 6:
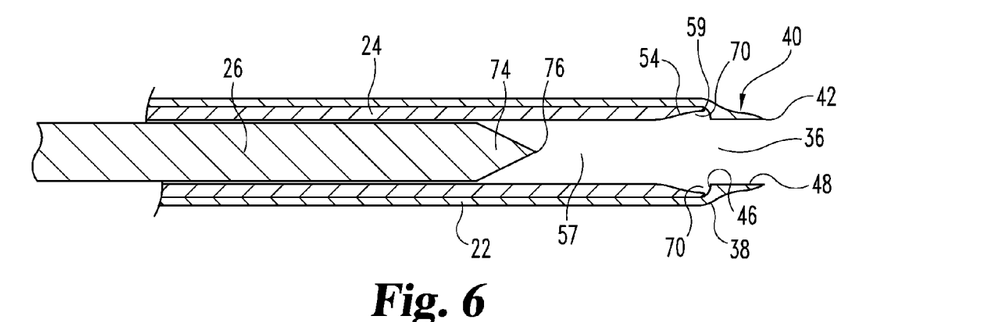
FIG. 6 is a side cross-sectional view of the embodiment shown in FIG. 1A, showing a different relative position of the components.

Cannula 24 and outer component 22 are fired together in this embodiment to a configuration with respect to mandrel 26 indicated in FIG. 6, in which a space is created in tip 40 and lumen 57. Tip 40 and fingers 54 are ahead of tip 74 of mandrel 26 by a predetermined distance corresponding to a length of tissue-core desired to be obtained in the biopsy. In particular embodiments, the predetermined distance (sample length) is between about 10 and 50 mm, such as about 20 mm.

Figure 7:
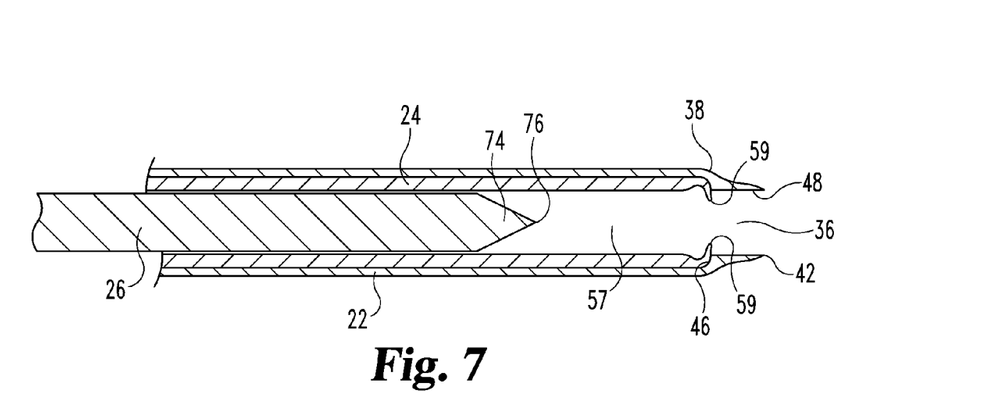
FIG. 7 is a side cross-sectional view of the embodiment shown in FIG. 1A, showing a different relative position of the components.

FIG. 7 is a representation of cannula 24 and outer component 22 in a second relative position. In a particular embodiment, cannula 24 is moved forward (distally) with respect to outer component 22, although other types of relative movement of cannula 24 and component 22 with respect to each other are contemplated. As cannula 24 is moved forward, points 59 of fingers 54 contact and are forced radially inward by surface 46 of boss 44. In particular embodiments, fingers 54 curve or curl along surface 46 so that points 59 face substantially radially (i.e. perpendicular to the longitudinal axis) in the second relative position. Force is applied by boss 44 against points 59 to bend points 59 as needed, rather than against a rear portion of fingers 54, so that bending occurs forward and little or no stress is applied to the root of the fingers 54. In one embodiment, the second relative position shown in FIG. 7 is the limit of relative forward movement of cannula 24, with no parts of fingers 54 (including points 59) contacting each other. The distance of travel of cannula 24 with respect to outer component 22 is small, for example less than the length of fingers 54, and in the embodiment of FIG. 7, not greater than half of the length of fingers 54.

In other embodiments, points 59 or other parts of fingers 54 may contact each other. In that second relative position, gaps 66 are not fully closed, even if points 59 or other parts of fingers 54 contact each other. At least a portion of gaps 66, such as that at the roots of fingers 54 (adjacent a vertex of elliptical gap 66), remains open. The lack of closure reduces or prevents compression of the tissue sample along a substantial portion of the end of the sample, making more of the sample useful for assaying.

The use of needle 20 will now be described in the context of obtaining a sample of soft tissue for testing purposes. It will be understood that methods for obtaining samples of other tissues or for other purposes are also contemplated.

The surgeon or other medical professional first determines a location in a patient, with its depth under the skin, from which a tissue sample is desired. In one embodiment, outer component 22, cannula 24 and mandrel 26 of needle 20 are in the relative position of FIGS. 1 and 1A, in which fingers 54 are proximal of surface 46 of boss 44. In that state, the medical professional places the distal end of needle 20 (tip 74 of mandrel 26, in this embodiment) against the skin at a place proximate to the desired location, and inserts needle 20. Tip 74, assisted by the tapered exterior of tip 40 and rounded portion 38 of component 22, force a path through the skin and subcutaneous tissue to a point in or just before the location from which a sample is to be taken. The configuration of tip 74, e.g. its greater angle with respect to the longitudinal axis than that of tapered surface of tip 40, tends to move tissue to the side rather than allowing it into needle 20 during this insertion. The path size and shape is determined by the outer configuration of outer component 22, and the path is not substantially larger than the outer diameter of component 22, reducing discomfort from the biopsy procedure.

Needle 20 is cocked, as noted above, by pulling plunger 82 of handle 28 until it catches. In the cocked state, in this embodiment, component 22 and cannula 24 are primed for firing forward together, with fingers 54 substantially linear with respect to the rest of cannula 24 and points 59 at or just behind surface 46. Lumen 36, 57 remain occupied by mandrel 26 in this state and is facing the tissue to be obtained, as does tip 40. In other embodiments, the cocking step primes only outer component 22 for firing forward.

Needle 20 is then fired, moving component 22 and cannula 24 in this embodiment forward quickly a distance dictated by the amount of tissue to be obtained, while mandrel 26 remains in place. That advancement results in cutting a profile (circular in the illustrated embodiment) through the tissue, with tissue entering lumen 36, 57 through tip 40 and beyond boss 44 and fingers 54 into cannula 24. The medical professional then advances cannula 24 within and with respect to component 22. As cannula 24 moves forward, points 59 are pressed against surface 46 of boss 44 and curve or are bent inward. Points 59 pinch or cut the tissue only at the distal end of the sample in this embodiment, and do not compress or crush a volume of tissue at or adjacent that distal end.

Figure 1:
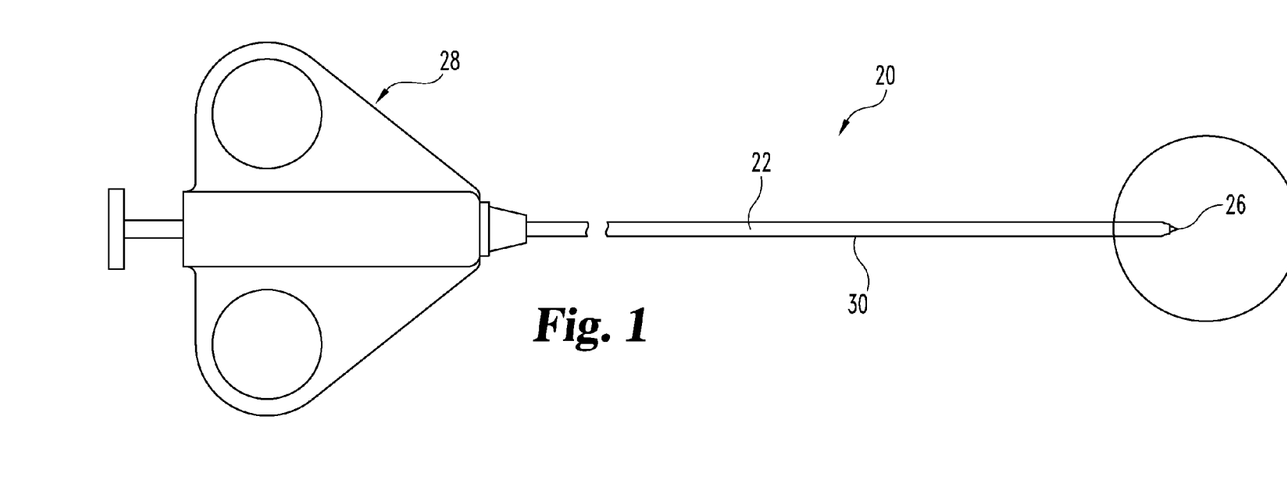
FIG. 1 is a plan view of an embodiment of a full-core biopsy needle.
Figure 1A:
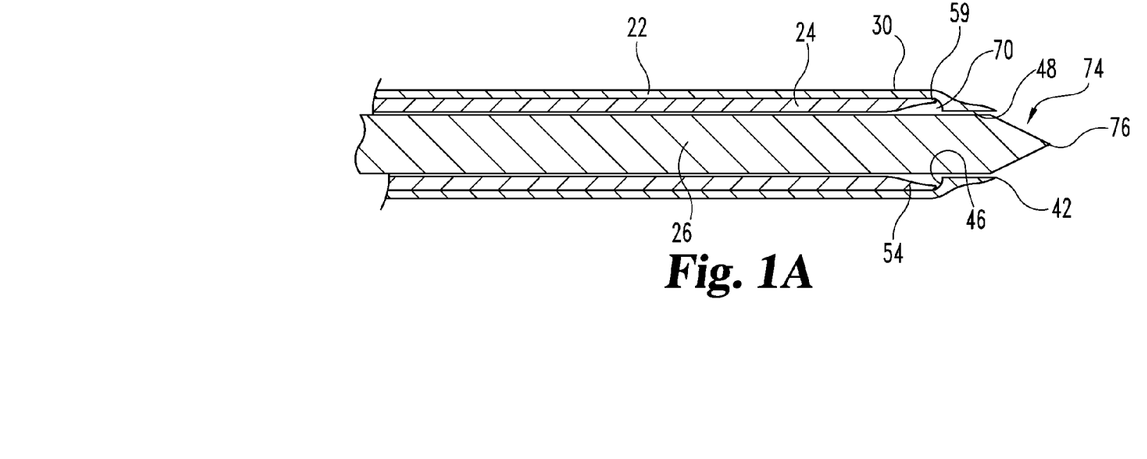
FIG. 1A is a close-up view in cross-section of the portion of the embodiment of FIG. 1 indicated by the circle in FIG. 1.
Figure 1B:
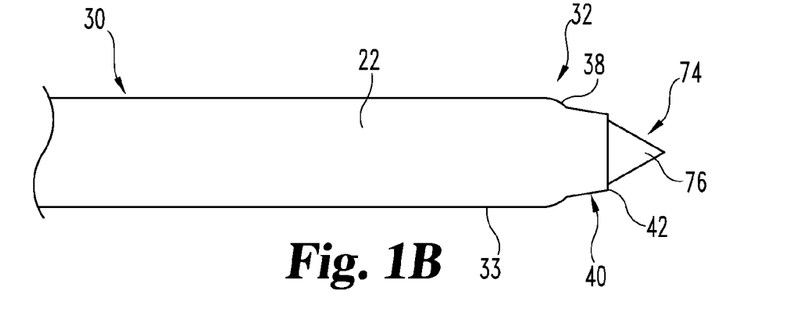
FIG. 1B is a close-up side view of the portion of the embodiment of FIG. 1 indicated by the circle in FIG. 1.

Fingers 54 weaken the connection between the sample within cannula 24 and adjacent tissue by pinching and/or cutting the tissue at the end of the sample, and they also provide a back-stop to prevent tissue from sliding or being pulled out of lumen 36, 57, and separation of the tissue inside lumen 44 from the remainder of the tissue is eased by the partial profile pinched or cut at the distal end of the tissue sample by the motion of finger 60 during firing. Points 59 do not extend longitudinally beyond boss 44 in this embodiment, so as to hole the great majority of tissue that enters needle 20, in some embodiments at least 90 percent of such tissue, and in others at least 80 percent of such tissue. Accordingly, less tissue must enter needle 20 to obtain a desired amount than prior devices. Such a configuration also does not score, crush or otherwise damage tissue on withdrawal of needle 20. Embodiments of needle 20 can also provide better security for the sample with less cutting or physical damage to tissue. For example, when needle 20 is withdrawn from the biopsy site, any resistance to the withdrawal by a tissue connection results in tissue inside cannula 24 pushing against points 59 and any addition portion of fingers 54 that extend radially into tissue. Fingers 54 are firmly backstopped by boss 44, so that any force applied by tissue within cannula 24 on fingers 54 cannot bend fingers 54 out of the way due to force from boss 44 through fingers 54 directly along the direction of needle withdrawal. The limited amount of fingers 54 that are curved downward into the tissue, indicated in the embodiment of FIG. 1, provide little opportunity for bending backward (e.g. along tip 40 as seen in FIG. 7). The configurations noted herein counteract force tending to bend fingers 54 away from their pinching or holding state and reopen lumen 36, 57, with the risk of losing some or all of the sample in lumen 36, 57.

While fingers 54 and points 59 curve in this embodiment along the curve into surface 46, depending on the relative stiffness of part or all of fingers 54, points 59 and/or additional parts of fingers 54 may not closely follow the curve and/or surface 46 as they move to or toward the extended or holding position (i.e. the second relative position between component 22 and cannula 24).

The elastic and low-profile nature of needle 20 and the flexibility and configuration of fingers 54 make taking multiple biopsy samples significantly easier and less traumatic.

Once a first sample is taken, as discussed above, needle 20 may be withdrawn from the body. Cannula 24 may be moved backward (proximally) with respect to component 20 and mandrel 26 may be moved forward (or needle 20 recocked), pushing tissue sample out tip 40. Recocked, needle 20 can be reinserted at the same or a different place. The steps noted above are repeated. In this way, as many samples may be taken as are desired.

As noted above, cannula 24 has a close fit with outer component 22 within its lumen 36, and mandrel 26 has a close fit within lumen 57 of cannula 24, with these items being slidable with respect to each other. By having both a "close fit" and slidability, it is meant that there is no substantial separation or gap between adjacent parts, as by an intermediate flange. As seen in the embodiments in the drawings, component 22 and cannula 24, and cannula 24 and mandrel 26, have a close and slidable fit at least along their respective distal ends, and in some embodiments that close and slidable fit extends along all or substantially all of their respective lengths. Such a configuration maximizes the amount of tissue obtained by a needle of particular outer diameter, by minimizing unused space in the needle, or conversely minimizes the external size of a needle needed to obtain a particular amount of tissue.

It will be understood that other embodiments may vary the operation of needle 20 described above. For example, an embodiment of needle 20 may be provided in which outer component 22 and cannula 24 are not shot forward together. One such embodiment would include a cannula 24 that does not move forward when needle 20 is fired and shoots forward outer component 22, i.e., outer component 22 is moved forward over cannula 24, and cannula 24 remains stationary during firing along with mandrel 26. In that case, boss 44 of component 22 would be separated from points 59 of cannula 24 by at least the distance outer component 22 is fired forward. A tissue mass of approximately diameter D1 (the internal diameter of tip 40 of component 22) would enter lumen 36 of component 22. Cannula 24 is then moved forward toward boss 44 over mandrel 26 and the tissue mass. As before, when points 59 of cannula 24 are forced against surface 46 of boss 44, points 59 deflect radially into the tissue mass.

Figure 8:
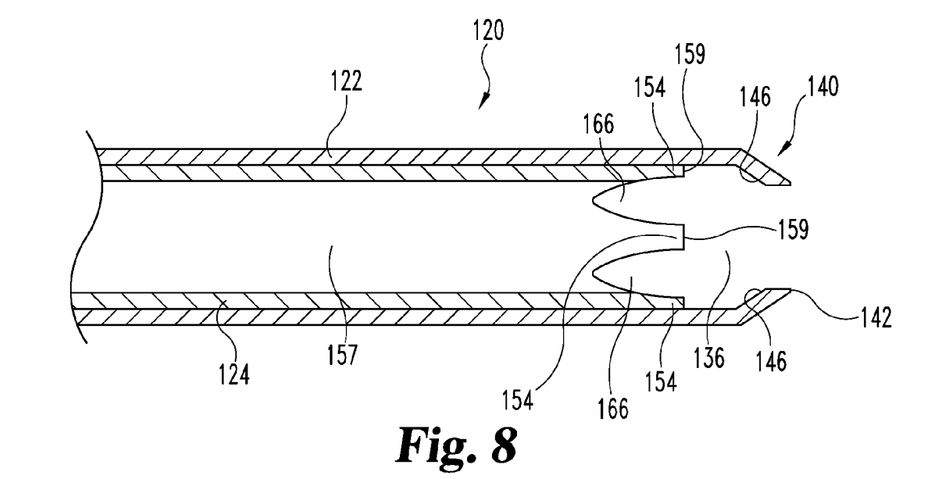
FIG. 8 is a side cross-sectional view of embodiments of structures in another embodiment of a full-core biopsy needle.
Figure 9:
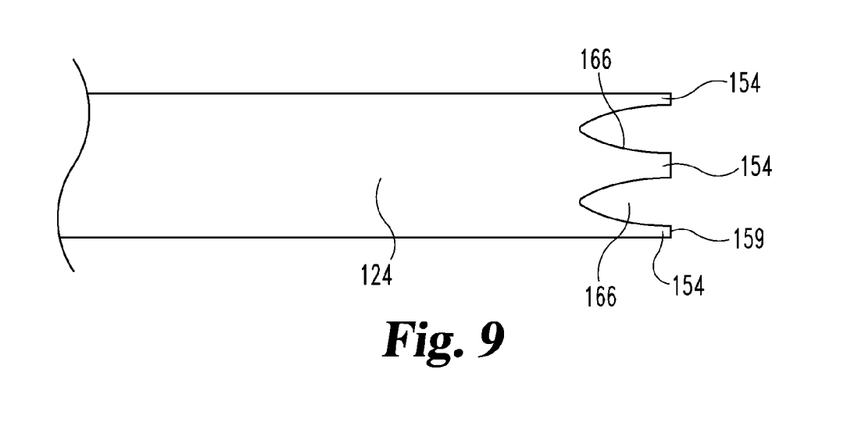
FIG. 9 is a side view of a portion of the structure shown in FIG. 8.

Other design possibilities exist, such as the embodiment of needle 120. As seen in FIGS. 8-9, an embodiment of outer needle component 122 is substantially identical to component 22, described above, but with a tip 140 that is somewhat differently configured. Items identified with a number that is 100 greater than another number used herein is identical or similar to a part discussed above with respect to needle 20. Outer component 122 has a substantially constant wall thickness surrounding a lumen 136 throughout most of its length. Tip 140 narrows or bends inward while maintaining the wall thickness in this embodiment, so that lumen 136 narrows from a first inner diameter to a second inner diameter. Tip 140 has an inner surface 146 that is angled with respect to the longitudinal axis, and in the illustrated embodiment the angle is approximately 45 degrees. It is believed that about a 45 degree angle is particularly effective in focusing force inward without excessive forward motion, as will be noted below. Tip 140 ends in an edge 142 that is substantially circular in the present embodiment.

Middle cannula 124 is very similar to cannula 24 described above, but has four fingers 154 in the illustrated embodiment. A lumen 157 extends through cannula 124 that has a substantially constant inner diameter until it reaches fingers 154 where the inner diameter enlarges. As with fingers 54, fingers 154 have an outer surface that coincides with the outer surface of the rest of cannula 124, and so the outer diameter measured across fingers 154 and the outer diameter of the rest of cannula 124 is constant. Fingers 154 thin from the inside to make them more flexible and to reduce interference as tissue enters lumen 136 and 157. In this embodiment, fingers 154 do not end in points but in linear or curvilinear edges 159 that lie in one plane. Like fingers 54, fingers 154 are separated by curved gaps 166 that remain at least partially open as fingers 154 are forced inward, as described below. Gaps 166 in this embodiment are part elliptical at the roots of fingers 154 and have a straight portion as fingers 154 approach edges 159. A mandrel, e.g. mandrel 26, may also be used with cannula 124 and component 122, as discussed above.

Operation of needle 120 is substantially the same as for needle 20. Once needle 120 is inserted into the patient, outer component 122 is fired forward over cannula 124 (or both component 122 and cannula 124 are fired forward over a mandrel) to cut a profile so that tissue enters lumen 136 in tip 140 and lumen 157 in cannula 124. The profile is substantially circular in this embodiment because edge 142 is circular. With tissue inside lumen 136, 157, cannula 124 is moved forward with respect to outer component 122. When fingers 154 reach surface 146, surface 146 acts as a boss and forces fingers 154 along surface 146 to pinch or cut tissue in a plane substantially coincidental with the plane of surface 146. Cannula 124 can be advanced so that fingers pinch or cut along that plane but do not contact each other, or may be advanced so that two or more edges 159 or other parts of fingers 154 contact each other. When fingers have been advanced as desired, withdrawal of needle 120 can take place, with fingers 154 backed up by surface 146 holding or pulling the tissue sample away from adjacent tissue.

Fingers 154 separated by gaps 166 act similarly to a collet structure, with edges 159 approaching each other when cannula 124 is advanced with respect to outer component 122. Fingers 154 are not intended to compress the tissue in lumens 136, 157 except to the extent tissue is pinched along the direction of travel of fingers 154. Gaps 166 relieve any pressure on the tissue sample that may exist, helping to retain the integrity and physical structure of the tissue sample, as gaps 66 do.

Outer components 22, 122, cannulas 24, 124 and mandrel 26 may be made of any of a number of sturdy materials or combinations of materials that provide sufficient rigidity for insertion into a patient for biopsy. Metals such as medical-grade stainless steel are appropriate, particularly for outer components 22, 122 and mandrel 26. Cannulas 24, 124 may be made of any of a variety of metals, for example, particularly those that are flexible with a high elastic limit in thin portions such as fingers 54, 154, so that fingers 54, 154 can be force to curve along surfaces yet elastically return to the initial configuration.

While the disclosure has been illustrated and described in detail in the drawings and foregoing description, the same is to be considered as illustrative and not restrictive in character, it being understood that only certain specific embodiments have been shown and that all changes and modifications that come within the spirit of the disclosure are desired to be protected.

What is claimed is:

1. A full-core biopsy needle, comprising:
    an outer tubular component having a body portion, a tip portion and a lumen through said body and tip portions, said component having a portion connecting said body portion and said tip portion, said connecting portion joining an outer wall of said body portion with a rounded portion that turns inward from the outer wall to form an external rounded corner and an internal proximal-facing surface, the rounded portion having a cross-section in a plane including the longitudinal axis of an arc of a circle, said rounded portion joining said tip portion at an end opposite the position where the rounded portion joins the body portion, said tip portion extending entirely around the longitudinal axis having an external diameter that decreases uniformly from the join with the rounded portion to a distal edge, said tip portion having a constant inner diameter between the proximal-facing surface of the rounded portion and the distal edge, the constant inner diameter of the tip portion being less than a constant inner diameter of the body portion, so that said lumen has a first diameter proximal of said proximal-facing surface and a second smaller uniform inner diameter extending distally from said proximal-facing surface, said lumen with said second smaller uniform diameter extending through said tip;

a middle cannula having a body portion and a tip portion, said tip portion having a plurality of fingers, at least a first and second of said fingers being separated by a gap, said middle cannula being within said lumen of said component, wherein said component and said cannula have a first relative position with said fingers proximal of said proximal-facing surface, and said cannula adapted to be moved distally with respect to said component into a second relative position, said second relative position being the limit of possible distal movement of said cannula with respect to said component and being a position in which at least said first and second fingers are deflected toward the longitudinal axis but not into the constant inner diameter of the tip portion by said proximal-facing surface, wherein in said second relative position at least a portion of said first and second fingers point toward each other but do not close the entirety of said gap.

2. The needle of claim 1, further comprising an internal mandrel extending through said middle cannula and being slidable with respect to said cannula and said component between a first limit in which a tip portion of said mandrel extends from said tip of said component and a second limit in which the tip portion of said mandrel is proximal of said fingers of said cannula by a predetermined distance prior to movement of said fingers with respect to said outer component.

3. The needle of claim 1, wherein said proximal-facing surface and said rounded portion are substantially radially aligned.

4. The needle of claim 1, wherein said fingers each have a respective external surface that is parallel to the longitudinal axis in said second relative position.

5. The needle of claim 1, wherein said first and second fingers have respective edges that together form a continuous substantially part-elliptical path.

6. The needle of claim 1, wherein said first and second fingers have distal linear or curvilinear edges.

7. The needle of claim 1, wherein said proximal-facing surface includes a surface that is substantially perpendicular to the longitudinal axis of said outer component.

8. The needle of claim 1, wherein said gap is substantially elliptical and said first and second fingers each have respective distal ends and proximal portions, a vertex of the substantially elliptical gap being between said fingers in said proximal portions, and when said outer component and said cannula are in said second relative position a portion of said gap adjacent said vertex remains open.

9. The needle of claim 1, wherein in said second relative position said first and second fingers contact each other and a portion of said gap is open between them.

10. The needle of claim 9, wherein said first and second fingers have respective distal ends, and said first and second fingers contact each other at or adjacent to said distal ends.

11. The needle of claim 1, wherein said first and second fingers are smaller than at least one gap between them.

12. The needle of claim 1, wherein said cannula has at least four fingers equidistantly spaced around said cannula.

13. The needle of claim 1, wherein said inward deflection of said fingers does not compress tissue within said fingers around the whole diameter of such tissue.

14. The needle of claim 1, wherein said fingers each have a distal end edge, and substantially all compression on tissue within said fingers is exerted by said distal end edges.

* * * * *